US00PP20261P2

(12) United States Plant Patent
Smith

(10) Patent No.: US PP20,261 P2
(45) Date of Patent: Sep. 1, 2009

(54) ***ASTER* PLANT NAMED 'YOHAZY'**

(50) Latin Name: *Aster hybrida*
Varietal Denomination: Yohazy

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,245

(22) Filed: Jun. 16, 2008

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent L Bell
(74) *Attorney, Agent, or Firm*—C. A. Whealy

(57) ABSTRACT

A new and distinct cultivar of *Aster* plant named 'Yohazy', characterized by its upright, uniform and mounded plant habit; freely branching growth habit; dark green-colored foliage; uniform and freely flowering habit; natural flowering season mid-September in the northern hemisphere; daisy-type inflorescences with dark pink-colored ray florets that resist fading over time; and good garden performance.

1 Drawing Sheet

Botanical designation: *Aster hybrida.*
Cultivar denomination: 'Yohazy'.

BACKGROUND OF THE INVENTION

The present invention relates to a new and distinct cultivar of *Aster* plant, botanically known as *Aster hybrida* and hereinafter referred to by the name 'Yohazy'.

The objective of the breeding program is to create new potted *Aster* cultivars with uniform and rounded plant growth habit, good vigor and strong branching habit, numerous inflorescences, desirable and unique ray floret color and good garden performance.

The new *Aster* originated from an open-pollination in August, 2003 in Salinas, Calif. of *Aster hybrida* 'Jenny', not patented, as the female, or seed, parent with an unknown *Aster hybrida* seedling selection, as the male, or pollen, parent. The new *Aster* was discovered and selected by the Inventor as a single flowering plant within the progeny of the stated open-pollination in a controlled greenhouse environment Alva, Fla. in October, 2004. The selection of this plant was based on its uniform plant growth habit, vigor and desirable ray floret color.

Asexual reproduction of the new *Aster* by vegetative tip cuttings was first conducted in a controlled greenhouse environment in Alva, Fla. in December, 2004. Asexual reproduction by cuttings has shown that the unique features of this new *Aster* are stable and reproduced true to type in successive generations.

SUMMARY OF THE INVENTION

Plants of the new *Aster* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yohazy'.

These characteristics in combination distinguish 'Yohazy' as a new and distinct potted *Aster* cultivar:

1. Upright, uniform and mounded plant habit.
2. Freely branching growth habit.
3. Dark green-colored foliage.
4. Uniform and freely flowering habit.
5. Natural flowering season mid-September in the northern hemisphere.
6. Daisy-type inflorescences with dark pink-colored ray florets that resist fading over time.
7. Good garden performance.

Plants of the new *Aster* differ from plants of the female parent, 'Jenny', in the following characteristics:

1. Plants of the new *Aster* are smaller and fuller than plants of 'Jenny'.
2. Plants of the new *Aster* have slightly smaller inflorescences than plants of 'Jenny'.
3. Ray florets of plants of the new *Aster* are slightly lighter in color than ray florets of plants of 'Jenny'.
4. Inflorescences of plants of the new *Aster* have better postproduction longevity than inflorescences of plants of 'Jenny'.

Plants of the new *Aster* can be compared to plants of *Aster hybrida* 'Winston Churchill', not patented. In side-by-side comparisons conducted in Alva, Fla., plants of the new *Aster* differed from plants of 'Winston Churchill' in the following characteristics:

1. Plants of the new *Aster* were smaller and fuller than plants of 'Winston Churchill'.
2. Plants of the new *Aster* had smaller inflorescences than plants of 'Winston Churchill'.

Plants of the new *Aster* can be compared to plants of *Aster novibelgii* 'Loke Viking', disclosed in U.S. Plant Pat. No. 10,359. In side-by-side comparisons conducted in Alva, Fla., plants of the new *Aster* differed from plants of 'Loke Viking' in the following characteristics:

1. Plants of the new *Aster* were smaller and fuller than plants of 'Loke Viking'.
2. Plants of the new *Aster* were stronger than plants of 'Loke Viking'.
3. Plants of the new *Aster* had smaller inflorescences than plants of 'Loke Viking'.
4. Plants of the new *Aster* had lighter-colored ray florets than plants of 'Loke Viking'.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster*.

The photograph at the bottom of the sheet comprises a side perspective view of a typical flowering plant of 'Yohazy' grown in a container.

The photograph at the top of the sheet is a close-up view of typical inflorescences of 'Yohazy'.

DETAILED BOTANICAL DESCRIPTION

The aforementioned photographs and following observations and measurements describe plants grown during the fall in Alva, Fla. in a polycarbonate-covered greenhouse and under conditions and practices which approximate those generally used in commercial potted *Aster* production. During the production of the plants, day temperatures ranged from 27° C. to 32° C. and night temperatures ranged from 16° C. to 24° C. Plants were grown in 10-cm containers and were pinched two times. Plants were two months from planting when the description and photographs were taken. In the following description, color references are made to The Royal Horticultural Society Colour Chart, 1995 Edition, except where general terms of ordinary dictionary significance are used.

Botanical classification: *Aster hybrida* 'Yohazy'.

Parentage:

*Female, or seed, parent.*—*Aster hybrida* 'Jenny', not patented.

*Male, or pollen, parent.*—Unknown *Aster hybrida* seedling selection, not patented.

Propagation:

*Type.*—Terminal vegetative cuttings.

*Time to initiate roots.*—About ten days at average temperatures of 22° C.

*Time to produce a rooted young plant.*—About 16 to 18 days at average temperatures of 22° C.

*Root description.*—Fine, fibrous; white in color.

*Rooting habit.*—Freely branching.

Plant description:

*Appearance.*—Herbaceous daisy-type potted *Aster*. Upright growth habit; inverted triangle with uniformly mounded crown. Strong and freely branching growth habit with about twelve primary lateral branches each with numerous secondary and tertiary branches; dense and full plants. Vigorous growth habit.

*Plant height.*—About 30 cm.

*Plant width.*—About 23 cm.

*Lateral branches.*—Length: About 23 cm. Diameter: About 2.5 mm. Internode length: About 1.2 cm. Strength: Strong. Texture: Sparsely pubescent; longitudinally ridged. Color: Close to 147A.

Foliage description:

*Arrangement.*—Alternate, simple; sessile.

*Length.*—About 4 cm.

*Width.*—About 1 cm.

*Shape.*—Lanceolate to narrowly deltoid.

*Apex.*—Acute.

*Base.*—Rounded; slightly clasping.

*Margin.*—Entire.

*Texture, upper and lower surfaces.*—Smooth, glabrous.

*Venation pattern.*—Pinnate, reticulate.

*Color.*—Developing foliage, upper surface: Close to 147A. Developing foliage, upper surface: Close to 137A. Fully expanded foliage, upper surface: Close to 139A; venation, close to 137B. Fully expanded foliage, lower surface: Close to 137A; venation, close to 137B.

Inflorescence description:

*Appearance.*—Daisy-type inflorescence form with lanceolate-shaped ray florets. Inflorescences borne on terminals above and beyond the foliage. Disk and ray florets arranged acropetally on a capitulum. Inflorescence not fragrant.

*Flowering response.*—Under natural conditions, plants flower in mid-September in the Northern Hemisphere. Inflorescences persistent. Inflorescences last about two weeks on the plant.

*Quantity of inflorescences.*—Freely flowering, about 16 to 17 inflorescences and inflorescence buds per lateral stem.

*Inflorescence bud.*—Height: About 1.4 cm. Diameter: About 7 mm. Shape: Oblong. Color: Close to 78C.

*Inflorescence size.*—Diameter: About 2.9 cm. Depth (height): About 1.5 cm. Diameter of disc: About 1.1 cm. Receptacle height: About 8 mm. Receptacle diameter: About 5 mm. Receptacle color: Close to 137A.

*Ray florets.*—Length: About 1.5 cm. Width: About 2 mm. Shape: Lanceolate. Apex: Acute. Base: Acute to attenuate. Margin: Entire. Texture, upper and lower surfaces: Smooth, glabrous, satiny. Orientation: Initially upright, then about 90° from vertical. Number of ray florets per inflorescence: About 28 arranged in about two whorls. Color: When opening and fully opened, upper surface: Close to 78A; color resists fading. When opening and fully opened, lower surface: Close to 78C.

*Disc florets.*—Arrangement: Massed at center of receptacle. Shape: Tubular, elongated. Apex: Five-pointed. Length: About 9 mm. Width: About 2 mm. Number of disc florets per inflorescence: About 40. Texture: Smooth, glabrous. Color, immature: Apex: Close to 154A. Mid-section: Close to 1A. Base: Close to 1B. Color, mature: Apex: Close to 185C. Mid-section: Close to 1B. Base: Close to 1C.

*Phyllaries.*—Number of phyllaries per inflorescence: About 30 arranged in about three whorls. Length: About 6 mm. Width: About 1 mm. Shape: Lanceolate. Apex: Acute. Base: Truncate. Texture, upper and lower surfaces: Smooth, glabrous. Color, upper and lower surfaces: Close to 139B.

*Peduncles.*—Length: First peduncle: About 1.3 cm. Fourth peduncle: About 2.6 cm. Seventh peduncle:

About 5 cm. Diameter (first peduncle): About 1 mm. Angle: Upright to about 30° to 45° from vertical. Strength: Strong, flexible. Texture: Sparsely pubescent; longitudinally ridged. Color: Close to 137B.

*Reproductive organs.*—Androecium: Present on disc florets only. Filament length: About 2 mm. Filament color: Close to 157A. Anther shape: Narrowly elongated; flattened. Anther length: About 1 mm. Anther color: Close to 3A. Pollen amount: Scarce. Pollen color: Close to 3A. Gynoecium: Present on both ray and disc florets. Pistil length: About 8 mm. Stigma shape: Bi-parted. Stigma color: Close to 1B. Style length: About 6 mm. Style color: Close to 1C. Ovary color: Close to 1D.

*Seed/fruit.*—Seed and fruit production have not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures from about 2° C. to about 38° C.

It is claimed:

1. A new and distinct *Aster* plant named 'Yohazy' as illustrated and described.

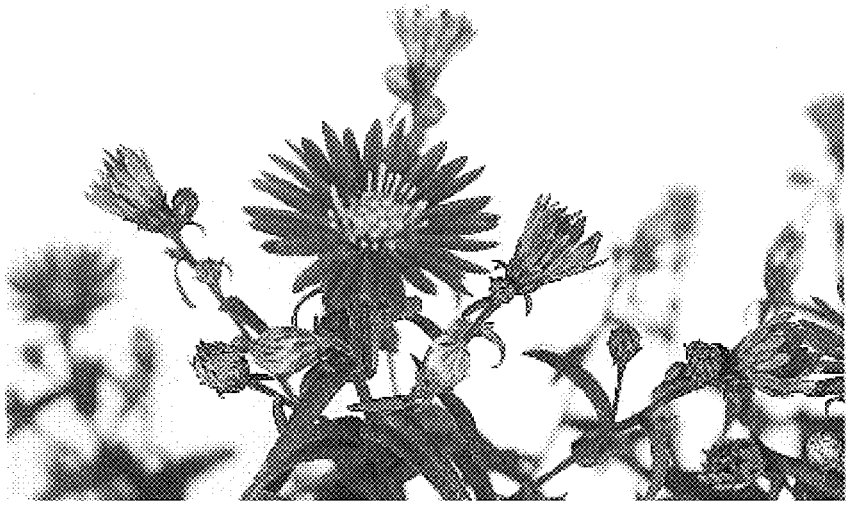
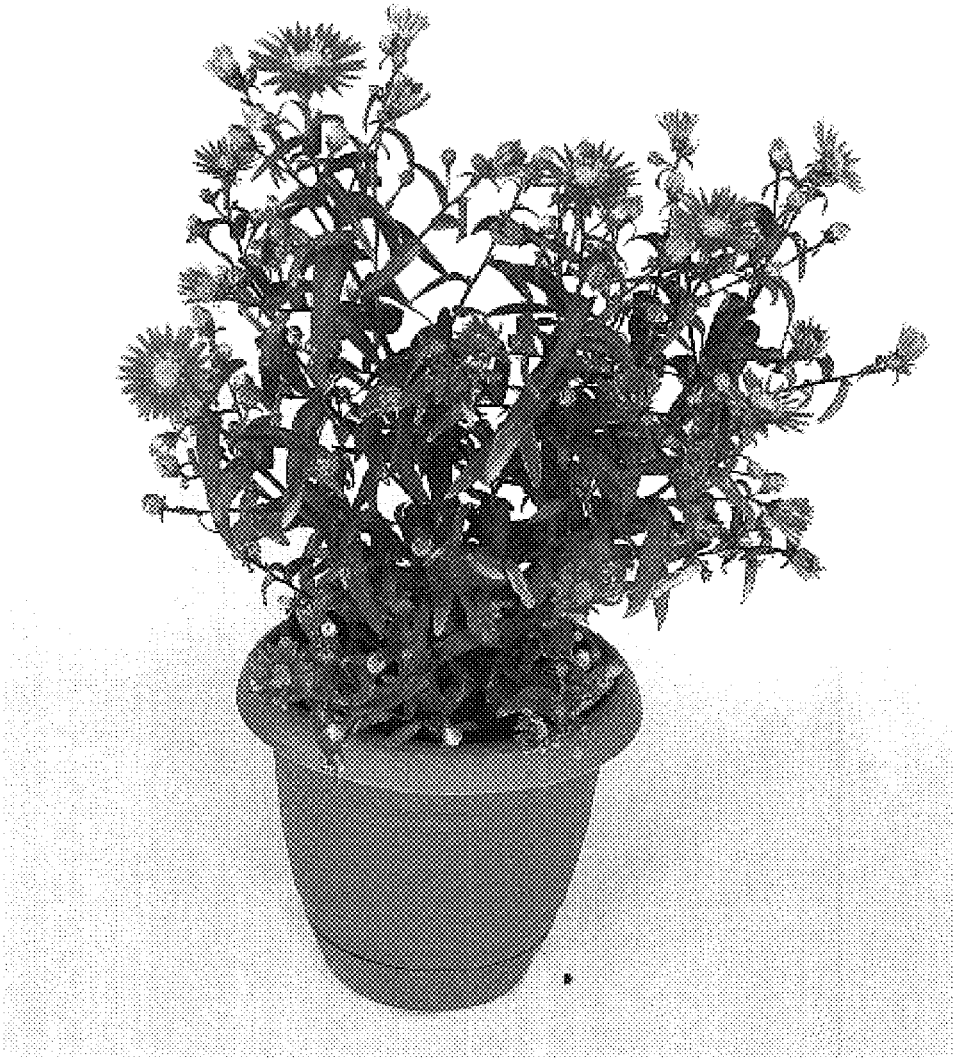

* * * * *